US006756041B2

(12) United States Patent
Lees et al.

(10) Patent No.: US 6,756,041 B2
(45) Date of Patent: Jun. 29, 2004

(54) PROCESS FOR PREPARING CONJUGATE VACCINES INCLUDING FREE PROTEIN AND THE CONJUGATE VACCINES, IMMUNOGENS, AND IMMUNOGENIC REAGENTS PRODUCED BY THIS PROCESS

(75) Inventors: Andrew Lees, Silver Spring, MD (US); James Mond, Jerusalem (IL)

(73) Assignee: Henry M. Jackson Foundation for the Advancement of Military Medicine, Rockville, MD (US)

(*) Notice: Subject to any disclaimer, the term of this patent is extended or adjusted under 35 U.S.C. 154(b) by 38 days.

(21) Appl. No.: 09/734,587

(22) Filed: Dec. 13, 2000

(65) Prior Publication Data

US 2002/0054879 A1 May 9, 2002

Related U.S. Application Data

(62) Division of application No. 09/003,155, filed on Jan. 6, 1998, now Pat. No. 6,248,334.
(60) Provisional application No. 60/034,653, filed on Jan. 8, 1997.

(51) Int. Cl.[7] ...................... A61K 39/02; A61K 39/385; C07K 16/00; C07K 14/00; C12P 21/08
(52) U.S. Cl. ...................... 424/236.1; 424/184.1; 424/194.1; 530/422; 530/330; 530/402; 530/403; 530/404; 530/405; 530/406; 530/407; 530/408; 530/409; 530/410; 530/411; 530/412; 530/414; 530/391.9; 530/810
(58) Field of Search ...................... 530/422, 330, 530/403, 404, 405, 406, 402, 407–412, 414, 391.9, 810; 424/236.1, 194.1, 184.1

(56) References Cited

U.S. PATENT DOCUMENTS

| 5,302,386 | A |   | 4/1994 | Kasper et al. |   |
|---|---|---|---|---|---|
| 5,585,100 | A | * | 12/1996 | Mond et al. | 424/193.1 |
| 5,651,971 | A | * | 7/1997 | Lees | 424/178.1 |
| 5,693,326 | A | * | 12/1997 | Lees | 424/178.1 |
| 5,849,301 | A |   | 12/1998 | Lees |   |
| 5,874,085 | A |   | 2/1999 | Mond et al. |   |
| 5,955,079 | A | * | 9/1999 | Mond et al. | 424/193.1 |
| 6,087,328 | A |   | 7/2000 | Lees |   |
| 6,146,902 | A | * | 11/2000 | McMaster | 424/193.1 |
| 6,149,911 | A | * | 11/2000 | Binz et al. | 424/192.1 |
| 6,224,880 | B1 | * | 5/2001 | Chan et al. | 424/193.1 |
| 6,248,334 | B1 | * | 6/2001 | Lees et al. | 424/184.1 |
| 6,284,250 | B1 | * | 9/2001 | Lees et al. | 424/193.1 |
| 6,299,881 | B1 | * | 10/2001 | Lees et al. | 424/146.1 |
| 6,309,646 | B1 | * | 10/2001 | Lees | 424/193.1 |
| 6,361,777 | B1 | * | 3/2002 | Hoogerhout | 424/184.1 |

FOREIGN PATENT DOCUMENTS

| CA | 2171942 |   | 3/1995 |
|---|---|---|---|
| EP | 0378881 | * | 7/1990 |
| WO | WO 96 29094 |   | 9/1996 |
| WO | WO 96 40242 |   | 12/1996 |
| WO | WO 9830239 |   | 7/1998 |

OTHER PUBLICATIONS

Shafer et al, Vaccine, 2001, 19:1547–1558.*
Meacle et al, J. of Membrane Science, 1999, 161:171–184.*
Lamb et al, J. of Chromatography, 2000, 894:311–318.*
Pawlowski et al, Vaccine, 2000, 18:1873–1885.*
Pawlowski et al, Vaccine, 1999, 17:1474–1483.*
Lees, et al., "Activation of Soluble Polysaccharides with 1–Cyano–4–Dimethylamino Pyridinium Tetrafluoroborate For Use in Protein–Polysaccharide Conjugate Vaccines and Immunological Reagents," Vaccine, vol. 14, No. 3, 1996, pp. 190–198.
Dick, et al., "Glyconjugates of Bacterial Carbohydrate Antigens: A Survey and Consideration of Design and Preparation Factors," Conjugate Vaccines (Eds. Cruse, et al.), Karger, Basel, 1989, pp. 48–114.
Peeters et al., "Pneumococcal conjugate vaccines," Immunology Letters, vol. 30, No. 2, 1991, pp. 267–274.
Cassels et al., "Antibody to N–Terminal Consensus Peptide is Cross–Reactive with all Six Members of the Enterotoxigenic E. coli CFA/I Family," Cytokines, Cholera, and the Gut, pp. 275–279.
Halista et al., Pediatric Research 43/4:496–503, 1998.
Akkoyunlu et al., "Biological Acitivty of Serum Antibodies to a Nonacylated Form of Lipoprotein D of Haemophilus influenzae," Infection & Immunity, vol. 64, 1996, pp. 4586–4592.

(List continued on next page.)

Primary Examiner—Nita Minnifield
(74) Attorney, Agent, or Firm—Finnegan, Henderson, Farabow, Garrett & Dunnter, LLP

(57) ABSTRACT

A process for preparing a protein-polysaccharide conjugate includes reacting a protein with a polysaccharide to produce a mixture including a protein-polysaccharide conjugate and free protein. At least one unreacted reagent or low molecular weight component is removed from this mixture, without removing all of the free protein, to provide a purified mixture that contains the protein-polysaccharide conjugate and free protein. This purified mixture can be used as a conjugate vaccine, immunogen, or immunological reagent. Keeping the free protein in the purified mixture with the conjugate saves time and money in the conjugate production process. In another aspect of the invention, the purified mixture of the protein-polysaccharide conjugate and free protein is reacted with a hapten to produce a conjugate mixture including a hapten-protein conjugate and a hapten-protein-polysaccharide conjugate. Alternatively, the hapten-protein conjugate can be prepared first, this conjugate then reacting with a polysaccharide reagent to produce the conjugate mixture. This conjugate mixture can be treated further to remove the free hapten. The conjugate mixture, including the hapten-protein-polysaccharide conjugate and the hapten-protein conjugate, also can be used as a conjugate vaccine, immunogen, or immunological reagent.

7 Claims, No Drawings

OTHER PUBLICATIONS

Ellis et al., (Editors), Development and Clinical Uses of *Haemophilus B*. Conjugate Vaccines, Marcel Dekker, New York, 1994.

Lees et al., "Enhanced Immunogenicity of Protein–Dextran Conjugates: I. Rapid Stimulation of Enhanced Antibody Responses to Poorly Immunogenic Molecules," Vaccine, vol. 12, No. 13, 1994, pp. 1160–1166.

Martin, E.W., Remington's Pharmaceutical Sciences, $18^{th}$ Edition, 1994, pp. 1435–1711, 1389–1404.

Cruse et al. (Editors), Conjugate Vaccines, Karger, Basel, 1989.

Monsigny et al., "Colorimetric Determination of Neutral Sugars by a Resorcinol Sulfuric Acid Micromethod," Anal. Biochem. vol. 175, 1988, pp. 525–530.

Vidal & Franci, Letter to the Editors, J. Immunol. Meth., vol. 86, 1986, pp. 155–156.

* cited by examiner

PROCESS FOR PREPARING CONJUGATE VACCINES INCLUDING FREE PROTEIN AND THE CONJUGATE VACCINES, IMMUNOGENS, AND IMMUNOGENIC REAGENTS PRODUCED BY THIS PROCESS

RELATED APPLICATION DATA

This application is a divisional of U.S. Non-Provisional Patent Application No. 09/003,155 (now U.S. Pat. No. 6,248,334), filed Jan. 6, 1998 which claims priority benefits under 35 U.S.C. § 119 based on U.S. Provisional Patent Application No. 60/034,653, filed Jan. 8, 1997, which applications are incorporated herein by reference.

BACKGROUND OF THE INVENTION

Vaccines have been very effective in protecting people from a wide variety of diseases, whether caused by virus, bacteria, or fungus. The ability of vaccines to induce specific protection against such a wide range of pathogenic organisms results from their ability to stimulate specific humoral antibody responses, as well as cell-mediated responses. This invention relates to a process for preparing such vaccines, and particularly to a process for making protein-polysaccharide conjugates that are used in preparing vaccines, immunogens, and other valuable immunological reagents. The invention further relates to the vaccines, immunogens, and immunological reagents produced from the conjugates made according to the invention.

Certain agents can stimulate an immune response with minimal chemical modifications, for example, tetanus toxoid, which is immunogenic even in the absence of an adjuvant. Other important agents are either non-immunogenic or poorly immunogenic, but they can be converted into immunogenic molecules or constructs, in which form they can induce vigorous immune responses. For example, most polysaccharides are poorly immunogenic. After they are coupled to proteins, however, the resulting construct becomes immunogenic. The conjugation of proteins to polysaccharides converts the polysaccharide from a weakly immunogenic T-cell independent antigen to a T-cell dependent antigen that recruits T-cell help, and thus stimulates heightened immune responses. Note the discussion by J. M. Cruse, et al. (Editors), *Conjugate Vaccines*, Karger, Basel, (1989); and R. W. Ellis, et al. (Editors), *Development and Clinical Uses of Haemophilus B Conjugate Vaccines*, Marcel Dekker, New York (1994). These books are entirely incorporated herein by reference.

Conjugation of a protein and a polysaccharide can provide other advantageous results. For example, it has been found that protein-polysaccharide conjugates enhance the antibody response not only to the polysaccharide component, but also to the protein component. This effect is described, for example, in the dual conjugate patent application of Mond and Lees, U.S. patent application Ser. No. 08/402,565 (filed Mar. 13, 1995); application Ser. No. 08/444,727 (filed May 19, 1995); and application Ser. No. 08/468,060 (filed Jun. 6, 1995). These patent applications each are entirely incorporated herein by reference. This effect also is described in A. Lees, et al., "Enhanced Immunogenicity of Protein-Dextran Conjugates: I. Rapid Stimulation of Enhanced Antibody Responses to Poorly Immunogenic Molecules," *Vaccine*, Vol. 12, No. 13, (1994), pp. 1160–1166. This article is entirely incorporated herein by reference.

Noting at least some of the advantageous results obtained using protein-polysaccharide conjugates, researchers have developed various techniques to facilitate coupling of proteins and polysaccharides. Note W. E. Dick, et al., "Glyconjugates of Bacterial Carbohydrate Antigens: A Survey and Consideration of Design and Preparation Factors," *Conjugate Vaccines* (Eds. Cruse, et al.), Karger, Basel, 1989, beginning at page 48. This article also is entirely incorporated herein by reference. As one example of a protein-polysaccharide coupling technique, the use of organic cyanylating reagents, such as 1-cyano-4-(dimethylamino)-pyridinium tetrafluoroborate, also called "CDAP" in this patent application, has been developed. These reagents activate polysaccharides and facilitate coupling of polysaccharides to proteins for conjugate vaccines. The activated polysaccharides can be directly or indirectly coupled to proteins. The use of CDAP and other organic cyanylating reagents is described in the following U.S. Patent and Patent Applications of Andrew Lees: U.S. patent application Ser. No. 08/124,491 (filed Sep. 22, 1993, now abandoned), U.S. Pat. No. 5,651,971; and U.S. patent application Ser. No. 08/482,666 (filed Jun. 7, 1995). This U.S. patent and the patent applications each are entirely incorporated herein by reference. The use of CDAP also is described in Lees, et al., "Activation of Soluble Polysaccharides with 1-Cyano-4-Dimethylamino Pyridinium Tetrafluoroborate For Use in Protein-Polysaccharide Conjugate Vaccines and Immunological Reagents," *Vaccine*, Vol. 14, No. 3 (1996), pp. 190–198. This article also is entirely incorporated herein by reference. Other techniques for coupling proteins and polysaccharides using homobifunctional or heterobifunctional vinylsulfones are described in U.S. Provisional Patent Appln. No. 60/017,103 filed on May 9, 1996, and U.S. patent application Ser. No. 08/852,733 filed on May 7, 1997, each in the name of Andrew Lees. Protein/polysaccharide coupling using uronium salts and haloacyl reagents is described in U.S. Provisional Patent Appln. Nos. 60/041,781 (filed Mar. 24, 1997) and No. 60/042,379 (filed Apr. 24, 1997). These patent applications also are entirely incorporated herein by reference.

In the production of protein-polysaccharide conjugate vaccines, a major cost and time consuming step lies in the separation of the free protein (i.e., the unreacted or non-conjugated protein) from the conjugated protein-polysaccharide product. This separation, which is also called "fractionation," usually is accomplished using a column chromatographic technique (e.g., size exclusion chromatography) or an ultrafiltration process. These protein separation processes significantly increase the time and expense involved in producing protein-polysaccharide conjugate vaccines. Under the good manufacturing procedure ("GMP") guidelines, a dedicated (and expensive) chromatography column normally is needed for each type of vaccine conjugate to prevent contamination of the product.

In addition to the increased cost and time, this protein separation step often results in a significant loss of the desired protein-polysaccharide conjugate material. Additionally, the free protein material that is collected in this separation step typically is discarded. These factors further increase the costs involved in preparing a protein-polysaccharide conjugate vaccine.

SUMMARY OF THE INVENTION

It is an object of this invention to provide a method for producing protein-polysaccharide conjugates that avoids the problems and disadvantages described above. These conjugates can be used as intermediate materials in the production of other conjugates, such as hapten-protein-polysaccharide conjugates. It is a further object of this invention to provide vaccines, immunogens, and other immunological reagents that are produced by this method.

In one embodiment, this invention relates to a process for preparing a protein-polysaccharide conjugate. This process includes reacting a protein with a polysaccharide to produce a mixture including a protein-polysaccharide conjugate and free protein. At least one unreacted reagent or low molecular weight component is removed from this mixture to provide a purified mixture containing the protein-polysaccharide conjugate and free protein.

In another embodiment of the invention, a hapten-protein-polysaccharide conjugate is prepared. In this process, a purified mixture including a protein-polysaccharide conjugate and free protein first is produced in the manner described above. Thereafter, a hapten (e.g., a peptide) is reacted with the purified mixture of the protein-polysaccharide conjugate and the free protein, thereby providing a conjugate mixture including a hapten-protein conjugate, hapten-protein-polysaccharide conjugate, and free hapten. This conjugate mixture can be treated further to remove the free hapten to thereby provide a purified conjugate mixture including the hapten-protein-polysaccharide conjugate and the hapten-protein conjugate.

As another alternative, a hapten-protein conjugate first can be produced. As noted above, the hapten can be, for example, a peptide. The excess free protein and/or free hapten optionally can be removed at this stage. Thereafter, this conjugate, present in excess, is reacted with a polysaccharide to form a hapten-protein-polysaccharide conjugate. It is not necessary to remove the excess hapten-protein conjugate from the resulting conjugate mixture. The conjugate mixture includes the hapten-protein conjugate and the hapten-protein-polysaccharide conjugate.

The invention further relates to the protein-polysaccharide conjugate and free protein mixture, as well as the hapten-protein-polysaccharide conjugate and hapten-protein conjugate mixture, made by the processes of the invention. In addition to vaccines, the conjugates according to this invention can be used as immunogens or immunological reagents.

DETAILED DESCRIPTION OF THE INVENTION

As described above, various techniques and processes for producing protein-polysaccharide conjugates, immunogens, immunological reagents, and vaccines are known. Typically, separating the non-conjugated free protein from the conjugated protein-polysaccharide product represents a major cost in conjugate vaccine production. This separation can be accomplished, for example, using column chromatography (e.g., size exclusion chromatography) or ultrafiltration. These protein separation steps significantly increase the time and expense involved in producing protein-polysaccharide conjugate vaccines, not only because of the time and expense involved in the separation step, but also because of the expense involved in providing a separate chromatography column for each different type of vaccine conjugate. Additionally, costs are increased because the free protein separation step often results in a significant loss of the desired protein-polysaccharide conjugate material.

In some instances, there is no alternative to removing the free protein from the conjugate product. Certain conjugation techniques damage the protein and thereby significantly reduce its antigenicity and immunogenicity. An example of such a technique is carbodiimide coupling of tetanus toxoid to PRP (a capsular polysaccharide from *Haemophilus influenza* type b). If free protein reduces the immunogenicity of the resulting conjugate, then the unconjugated protein needs to be removed from the conjugate product. Non-immunogenic proteins, such as bovine serum albumin ("BSA"), also may inhibit the anti-protein response to BSA-polysaccharide. In this instance, the unreacted protein should be removed from the conjugate product. As noted above, column chromatography or ultrafiltration typically can be used to remove the unreacted free protein.

Applicants have observed, however, that many other conjugation techniques do not damage the free protein. Examples of these techniques include conjugating via CDAP activation of the polysaccharide or coupling via thio-ether linked spacers. When the free protein is not damaged during conjugation, typically there is no reduction in its antigenicity or its immunogenicity.

In new generation vaccines, the antibody response to the protein also is important. One example is the lipoprotein D-PRP conjugate vaccine ("PRP" means "polyribosylribitol phosphate"). In this vaccine, the anti-PRP response is for Haemophilus type b, and the lipoprotein D response is expected to provide protection against non-typable Haemophilus (ref.: Akkoyunlu, et al., *Infection & Immunity*, Vol. 64, 1996, beginning at pg. 4586, which article is entirely incorporated herein by reference). In still other instances, the immune response to the protein carrier coupled to the polysaccharide is not considered critical, per se, but if an immune response is generated to this carrier, it may be helpful. An example of this is the combination vaccine including a tetanus toxoid ("TT")-PRP conjugate vaccine mixed with tetanus toxoid, pertussis and diphtheria toxoid (Hib DPT).

Considering these observations, applicants have developed an improved method for manufacturing conjugate vaccines. In this method, instead of removing the unconjugated or free protein that remains after producing the protein-polysaccharide conjugates, only certain reagents and low molecular weight polysaccharides are removed from the reaction mixture. The free unconjugated protein remains in solution with the protein-polysaccharide conjugate. By this improved process, the resulting conjugate vaccine can have improved immune response due to the free protein while reducing production costs, equipment costs, and time expenditure in conjugate production.

In addition to the protein and polysaccharide components, during conjugate production, various reagents and low molecular weight components typically are present in the reaction mixture (e.g., cross-linking reagents, buffering components, low molecular weight oligosaccharides, etc.). These excess reagents and low molecular weight components can be removed from the reaction mixture by any suitable process known in the art, such as through dialysis, ultrafiltration, or desalting columns. Typically, at least any materials having a molecular weight below 10,000 are removed, and preferably, materials having a molecular weight below 30,000 are removed. This removal provides a purified mixture including the protein-polysaccharide conjugate and the free protein. Preferably, little or no free protein is removed from the mixture during this initial purification step. The purified mixture preferably contains protein-polysaccharide conjugate and free protein in a weight ratio of 0.95 mg conjugated protein per 0.05 mg free protein to 0.1 mg conjugated protein per 0.9 mg free protein, and advantageously this ratio is in the range of 0.7 mg conjugated protein per 0.3 mg free protein to 0.95 mg conjugated protein per 0.05 mg free protein. These ratios correspond to 5–90% free protein, and preferably 5–30% free protein, by weight, based on the entire protein content. While these free protein ratios are preferred, with high conjugate yield during the conjugation reaction, the free protein content can be as low as 1% in the invention, such that the purified mixture contains 1–90% free protein, with 1–30% free protein preferred (based on the entire protein content). In one embodiment of the invention, the ratio of conjugated to free protein is about 1:1, by weight.

The purified mixture, including the free protein and the protein-polysaccharide conjugate, can be combined with a pharmaceutically acceptable medium or delivery vehicle. As will be discussed in more detail below, the pharmaceutically acceptable medium or delivery vehicle can include at least one member selected from the group consisting of water, petroleum oil, animal based oil, vegetable oil, peanut oil, soybean oil, mineral oil, sesame oil, saline, aqueous dextrose, and glycerol solutions.

In accordance with the process of the invention, the polysaccharide can be activated, for example, using an organic cyanylating reagent during the step of producing the conjugate. Suitable cyanylating reagents include 1-cyano-4-(dimethylamino)-pyridinium tetrafluoroborate ("CDAP"), N-cyanotriethyl-ammonium tetrafluoroborate ("CTEA"), and p-nitrophenylcyanate. As noted above, the use of such organic cyanylating reagents is described in U.S. patent application Ser. No. 08/124,491 (filed Sep. 22, 1993, now abandoned), U.S. Pat. No. 5,651,971; and U.S. patent application Ser. No. 08/482,666 (filed Jun. 7, 1995). CDAP is particularly preferred as an organic cyanylating reagent.

The protein and polysaccharide also can be conjugated together via a spacer in the process according to the invention. As one example, a thio-ether spacer can be used in this process. Processes for using a spacer during production of a protein-polysaccharide conjugate, as noted above, are described in U.S. Provisional Patent Appln. No. 60/017,103 filed on May 9, 1996 and U.S. patent application Ser. No. 08/852,733 filed May 7, 1997. These applications describe, for example, the use of homobifunctional or heterobifunctional vinylsulfones to provide a spacer in the protein-polysaccharide conjugate. The protein and/or the polysaccharide can be derivatized or functionalized prior to the conjugation reaction procedure (e.g., with thiols, anines, or hydrazides). Other suitable protein/polysaccharide conjugation techniques for use with this invention are described, for example, in U.S. Provisional Patent Appln. Nos. 60/041,781 and 60/042,379, as mentioned above.

In another aspect of the invention., a hapten-protein-polysaccharide conjugate can be prepared using a mixture including a protein-polysaccharide conjugate and free protein produced in the manner described above. After the purified mixture containing the conjugate and the free protein is prepared, a hapten is reacted with the purified mixture to thereby provide a conjugate mixture including a hapten-protein conjugate and a hapten-protein-polysaccharide conjugate. This conjugate mixture can be treated further to remove the free hapten to thereby provide a purified conjugate mixture. This purified conjugate mixture can be mixed with a pharmaceutically acceptable medium or delivery vehicle.

The excess hapten can be removed from the conjugate mixture by any suitable process known in the art. As one specific example, the excess peptide is removed by dialysis to provide the purified conjugate mixture. Peptides are the particularly preferred haptens for use in this embodiment of the invention.

An alternative procedure for producing a conjugate mixture including a hapten-protein-polysaccharide conjugate and a hapten-protein conjugate is described below. A hapten-protein conjugate first is produced by reacting a hapten (such as a peptide) with a protein. The excess free protein and/or free hapten optionally (and preferably) is removed at this stage. Thereafter, this conjugate is reacted with a polysaccharide to form a hapten-protein-polysaccharide conjugate. In this reaction, the hapten-protein conjugate is used in excess to produce a conjugate mixture including the excess hapten-protein conjugate and a hapten-protein-polysaccharide conjugate. The purified conjugate mixture includes the hapten-protein conjugate and the hapten-protein-polysaccharide conjugate. This conjugate mixture can be combined with a pharmaceutically acceptable medium or delivery vehicle.

While any amount of protein can be included in the conjugates according to the invention, generally about 0.1 to 1.0 mg protein is present per mg polysaccharide in the conjugate mixture. Also, in conjugates that include peptides, generally there will be about 5–30 moles peptides per mole of protein.

The processes in accordance with the invention can be used on any suitable protein. Examples of suitable proteins include microbial proteins or bacterial proteins. Specific examples of suitable proteins include diphtheria, pertussis toxoid, lipoprotein D, lipoprotein OspA, tetanus toxoid, and gD protein (derived from herpes). Likewise, the processes of the invention can be used on any suitable polysaccharide, such as microbial polysaccharides, fungal polysaccharides, or bacterial polysaccharides. Specific examples of suitable polysaccharides include PRP, dextran, *Neisseria meningiditis* polysaccharide type C ("Neisseria PsC"), Vi antigen, and pneumococcal polysaccharide. Where a peptide or other hapten is included in the conjugate, any suitable peptide or other hapten can be used. Examples of suitable peptides include luteinizing hormone releasing hormone ("LHRH"); peptides derived from *E coli* bacteria (such as ETEC as described in "Antibody to N-Terminal Consensus Peptide is Cross-Reactive with all Six Members of the Entero-Enterotoxigenic *E coli* CFA/I Family," F. J. Cassels, et al., Abstract, 31 st Joint Conference, U.S./Japan Cooperative Medical Science Program, Kiwa Island, S.C., Dec. 1, 1995, which document is entirely incorporated herein by reference); and malaria derived peptides, such as SPf66. Other suitable proteins, polysaccharides and haptens for use in this invention are described in the above-noted U.S. patents and patent applications (e.g., U.S. patent application Ser. Nos. 08/124,491; 08/402,565; 08/444,727; 08/468,060; and 08/482,666, and U.S. Pat. No. 5,651,971).

This invention is particularly suitable for conjugation methods where the unconjugated protein is unmodified or minimally modified by the conjugation reaction procedure. CDAP coupling to produce the protein-polysaccharide conjugate is one such conjugation technique where the method according to the invention may be used. The method according to the invention, however, also may be used with other conjugation techniques where there are minimal modifications in the uncoupled protein. The unconjugated protein fraction in the protein-polysaccharide conjugate vaccine can be just as immunogenic as the native protein.

The process of the invention also can be used in producing a combination vaccine. Typically, to produce a combination vaccine, such as a vaccine including a tetanus toxoid ("TT")-PRP conjugate vaccine mixed with tetanus toxoid, pertussis and diphtheria toxoid (Hib DPT), one adds the conjugate back to free protein. In preparing this combination vaccine, first a purified TT-PRP conjugate is prepared (without free protein), and this material is then added to a tetanus toxoid, pertussis, diphtheria toxoid mixture to formulate the combination vaccine. In the process of the invention, however, this combination vaccine is produced by a different process. First, the tetanus toxoid and PRP are conjugated together. One vaccine manufacturer has indicated that it can obtain about 90% coupling efficiency of tetanus toxoid to PRP when CDAP is used to activate the polysaccharide and prepare the TT-PRP conjugates. Accordingly, after this conjugate production process, there may be about 10% free protein remaining in the mixture with the conjugate. In accordance with the process of the invention, there is no need to separate this free protein from the conjugate. Rather, only the excess CDAP and any other reagents are removed from the conjugate-free protein mixture (TT-PRP+TT). This conjugate-free protein mixture (TT-PRP+TT) is then added to a mixture including diphtheria toxoid and pertussis. If necessary or desired, the total amount of tetanus toxoid in the original conjugation reaction procedure can be adjusted so that a predetermined desired amount of tetanus toxoid is present in the final combination vaccine product. Alternatively, additional tetanus toxoid can be included in the diphtheria toxoid and pertussis mixture.

As another alternative, the process of the invention also can be used in the preparation of peptide-protein-polysaccharide conjugates or other hapten-protein-polysaccharide conjugates. Typically, when making such conjugates, a protein-polysaccharide conjugate first is prepared, and thereafter, a peptide is coupled to this conjugate. Applicants have observed, however, that the peptide-protein conjugate and the peptide-protein-polysaccharide conjugate mixture induces anti-polysaccharide, anti-protein, and anti-peptide responses. Accordingly, in an example of this process according to the invention, the protein-polysaccharide conjugate is produced, and the free protein is allowed to remain with the protein-polysaccharide conjugate. Thereafter, the peptide is reacted with this conjugate mixture, including the protein-polysaccharide conjugate and the free protein, to thereby produce a conjugate mixture including a peptide-protein-polysaccharide conjugate and a peptide-protein conjugate. The free peptide can be removed by dialysis to provide a purified conjugate mixture including the peptide-protein conjugate and the peptide-protein-polysaccharide conjugate. By eliminating the free protein removing step, the peptide-protein-polysaccharide conjugate can be produced in a more cost effective manner, and the resulting purified conjugate mixture produces enhanced anti-protein and anti-peptide responses.

Alternatively, as described above, a conjugate mixture including a peptide-protein conjugate and a peptide-protein-polysaccharide conjugate can be prepared by first conjugating the peptide and protein, and thereafter reacting this conjugate with a polysaccharide reagent.

The following Examples are provided to specifically illustrate the invention. Notably, these examples demonstrate that the presence of free protein with the conjugate need not markedly affect immunogenicity of the anti-protein response. These examples should be construed as illustrating the invention, and not as limiting the same.

EXAMPLE 1

For this example, tetanus toxoid ("TT") was conjugated to pneumoccocal 14 ("Pn14"). 37.5 μl of CDAP (100 mg/ml in acetonitrile) was added to 1 ml of Pn14 (present at 5 mg/ml in saline). After 30 seconds, 75 μl of triethylamine (0.2 M) was added, and additional triethylamine was added to maintain the pH in the range of 8 to 8.3. At 2.5 minutes, 5 mg of tetanus toxoid (at 16.8 mg/ml in saline) was added, and the reaction was allowed to proceed overnight at 4° C. The reaction was quenched by adding 200 μl of 2 M glycine at pH 8.

Part of the resulting reaction mixture was fractionated (to remove free protein) on an S400HR gel filtration column (Pharmacia), and the void volume fraction was obtained. The remainder of the reaction mixture solution was diluted to about 3 ml and dialyzed into phosphate buffered saline (PBS) using a "Slidelyzer" device (available from Pierce Chemical).

The resulting conjugates were centrifuged to remove aggregated material and sterile filtered using a Millex GV filter (available from Millipore Corp.). The following Table shows the conjugate yields.

TABLE 1

| Conjugate | Pn14 | Yield | TT | Yield |
| --- | --- | --- | --- | --- |
| Fractionated | 0.52 mg | 21% | 0.22 mg | 9% |
| Unfractionated | 1.11 mg | 44% | 1.2 mg | 48% |

Mice were immunized on Day 0 with 10 μg of Pn14-TT conjugate as produced above and with Pn-14 only and tetanus toxoid only as controls. On Day 14, the mice were bled and given a booster immunization with the same immunogen in the amount of 10 μg. The mice were bled again fourteen days later (Day 28).

Sera from each group of mice were pooled and assayed by ELISA ("enzyme-linked immunosorbent assay") for anti-Pn14 and anti-tetanus antibodies. A 0.5 OD cutoff was used for the ELISA titer. The test results are shown in the following Table.

TABLE 2

| | Anti-IgG Pn14 Titer | | Anti-IgG TT Titer | |
| --- | --- | --- | --- | --- |
| | Day 14 | Day 28 | Day 14 | Day 28 |
| Fractionated[1] | 1124 | 1828 | 43 | 615 |
| Unfractionated[2] | 2504 | 3168 | 308 | 10206 |
| Pn14 Only[3] | <100 | <100 | n.a.[4] | n.a. |
| TT Only[5] | n.a. | n.a. | 1793 | 35788 |

[1]4.3 μg tetanus toxoid, 10 μg Pn14.
[2]10.8 μg tetanus toxoid, 10 μg Pn14.
[3]10 μg Pn14.
[4]"n.a." means "not applicable".
[5]4.3 μg tetanus toxoid.

From the above Tables, it can be seen that the yield of the protein-polysaccharide conjugate is higher when fractionation is not performed. This shows that a significant amount of conjugate is lost during the fractionation process. Furthermore, both the anti-Pn14 and the anti-TT antibody titers are higher for the unfractionated conjugates as compared to the fractionated conjugates.

EXAMPLE 2

In this example, tetanus toxoid protein was coupled to Neisseria PsC polysaccharide, via a thio-ether spacer, to produce a conjugate. As a first step, the Neisseria PsC is derivatized and iodoacetylated. Neisseria PsC (from SmithKline Beecham, Rixensart, Belgium) was solubilized at 10 mg/ml in saline. 1 ml of 1 M 2-(N-Morpholino) ethanesulfonic acid ("MES") at pH 6 was added to 4 ml of the PsC. Hexanediamine was added as a solid to a concentration of 0.25 M, and Sulfo N hydroxysuccinimide was added to 5 mM. To start the derivatization, 500 μl 0.25 M (1-(3- dimethylaminopropyl) 3-ethyl carbodiimide hydrochloride ("EDC") in water was added. After 3.5 hours, the reaction mixture was desalted and concentrated by pressure filtration on an Amicon YM30 membrane. The $NH_2$-derivatized Neisseria PsC was found to contain 14 amines per 100 kDa Ps. The presence of amines was determined using a trinitrobenzenesulfonic (TNBS) acid assay, as described by J. Vidal and C. Franci, *J. Immunol. Meth.*, Vol. 86, pg. 155 (1986). The concentration of polysaccharides was determined using the resorcinol/sulfuric acid assay method of Monsigny, et al., *Anal. Chem.* Vol. 175, pg. 525 (1988), using a Neisseria PsC standard. These articles each are entirely incorporated herein by reference.

100 μl 0.75 M hydroxyethyl piperazine N'-2-ethane sulfonic acid ("HEPES" or "HE") and 5 mM ethylenediamine tetraacetate ("EDTA") (pH=7.3) were added to 1 ml of the $NH_2$-derivatized PsC (at 3.9 mg/ml) prepared above. 50 μl of 0.1 M n-hydroxysuccinimidyl iodoacetate ("SIA") coupling reagent (available from Pierce Chemical) also was added to the mixture. After about 2 hours, the polysaccharide was desalted on a P6DG column and concentrated to 250 μl using a Centricon 50 device (from Amicon). The resulting material was an iodoacetylated polysaccharide.

Tetanus toxoid was thiolated by adding 100 μl 0.75 M HEPES and 5 mM EDTA, at a pH of 7.3, to 238 μl tetanus toxoid (at 16.8 mg/ml) plus 10.7 μl of 25 mM N-succinimidyl 3-(2-pyridyldithio) propionate ("SPDP," available from Pierce Chemical) in dimethylformamide ("DMF"). The tetanus toxoid was obtained from SmithKline Beecham. At 1.5 hours, 200 μl of 1 M MES (pH 5.5) was added, followed by 27.5 μl 1 M DTT ("dithiothreitol") for 30 minutes. The resulting thiolated protein was desalted in phosphate buffered saline ("PBS") and concentrated to 300 μl using a Centricon 50 device (Amicon).

For conjugation, the thiolated tetanus toxoid protein and the iodoacetylated polysaccharide were combined, and 100 μl of 0.75 M HEPES and 5 mM EDTA (pH=7.3) were added. After an overnight reaction at 4° C., the reaction was quenched by adding 13 μl 10 mM mercaptoethanol for 1 hour, followed by 13 μl 0.5 M iodoacetamide for 10 minutes. The conjugate was fractionated by gel filtration on an S400HR column, equilibrated with PBS. The high molecular weight fraction was pooled and sterile filtered with a Millex GV device. The conjugate was assayed for protein using the BioRad assay and for polysaccharide using the resorcinol assay.

The conjugate resulting from the above-described reaction procedure had 10 μg of Neisseria PsC and 2.7 μg tetanus toxoid. Mice were immunized on Day 0 with this conjugate, with and without 7 μg of added tetanus toxoid present as a free protein. Each mouse was given a booster immunization of the same immunogen on Day 14. Fourteen days later (Day 28), the mice were bled ("pbd 14"). On Day 42, the mice were again bled and also were given another booster immunization ("boost") of the same immunogen. Finally, on Day 56, the mice were again bled ("pbbd14"). The blood samples were assayed for anti-Neisseria PsC Immunoglobulin G ("IgG") response by an enzyme-linked immunosorbent assay (ELISA) at 1:100. The test results are set forth in Table 3.

TABLE 3

Anti-Neisseria PsC IgG
(ELISA Absorbance @ 1:100)

| Immunogen | pbd 14 | boost | pbbd14 |
|---|---|---|---|
| TT-PsC | 0.461 | 0.479 | 0.863 |
| TT-PsC + Free TT | 0.676 | 0.804 | 0.922 |

The pbd 14 sera (from Day 28) was independently titered, at a 0.1 O.D., for IgG1, with the following results: (a) TT-PsC=34,109; and (b) TT-PsC plus TT=141,118.

These test results illustrate that the anti-polysaccharide response is not adversely affected, and indeed is enhanced in this case, by the presence of the free tetanus toxoid.

The collected sera also was assayed for anti-tetanus antibodies, and the test results are shown in the Table 4.

TABLE 4

Anti-Tetanus Toxoid IgG
(ELISA Absorbance @ 1:1000)

| Immunogen | pbd14 | boost | pbbd14 |
|---|---|---|---|
| TT-PsC | 0.631 | 0.452 | 1.226 |
| TT-PsC + Free TT | 0.996 | 0.897 | 1.619 |

The sera obtained above also was independently assayed by a third party, and the following results were obtained:

TABLE 5

| Immunogen | Anti-PsC titer | Bactericidal Titer |
|---|---|---|
| TT-PsC | 1283 | <1:10 |
| TT-PsC + Free TT | 826 | 1:80 |

The above data (Tables 3–5) indicate that injecting a mixture of free tetanus toxoid together with the tetanus toxoid-Neisseria PsC conjugate stimulated an anti-PsC response that was either comparable to or even higher than that stimulated by TT-PsC conjugate only. The data further indicates that the anti-protein response was increased when immunizing with the immunogen including the conjugate and the free protein. In Table 5, even though the anti-PsC titer was somewhat lower for the immunogen containing the free tetanus toxoid protein, the bactericidal titer was much higher, indicating the biological efficacy of the vaccine.

EXAMPLE 3

The free protein dosage response was tested in this Example. For this example, conjugates of Lipoprotein D ("LPD") and Pneumoccocal 14 ("Pn14," from SmithKline Beecham) were produced ("Pn14-LPD") using CDAP coupling chemistry, without free LPD protein (from SmithKline Beecham). Free protein was added to some conjugate samples in the indicated amounts shown below. Mice were immunized on Day 0 with 2.5 μg Pn14-LPD (per mouse) with: (a) 0 μg LPD as a free protein; (b) 0.25 μg LPD as a free protein; and (c) 2.5 μg LPD as a free protein. Each mouse was given a booster immunization of the same immunogen in the same dose on Day 22. Fourteen days later (Day 36), the mice were bled. The blood samples were assayed for anti-Pn14 IgG titer and anti-LPD titer responses. The test results are shown in Table 6.

TABLE 6

| Immunogen | Anti-Pn14 IgG Titer | Anti-LPD Titer |
| --- | --- | --- |
| Conjugate + 0 µg LPD | >44,547 | <61 |
| Conjugate + 0.25 µg LPD | 109,237 | 413 |
| Conjugate + 2.5 µg LPD | 27,298 | 424 |

When substituting PRP polysaccharide for Pn14 polysaccharide, following the same procedures described above, PRP-LPD conjugates, with and without free LPD protein, were produced. The following data was collected.

TABLE 7

| Immunogen | Anti-PRP Titer | Anti-LPD Titer |
| --- | --- | --- |
| Conjugate + 0 µg LPD | N.A.* | 29,272 |
| Conjugate + 0.25 µg LPD | N.A.* | >68,228 |
| Conjugate + 2.5 µg LPD | N.A.* | 37,297 |

*These mice respond poorly to PRP polysaccharide.

As illustrated in Table 6, the presence of the free LPD protein with the conjugate did not markedly affect the immunogenicity of the anti-Pn14 or anti-LPD responses. In fact, a relatively low amount of free LPD protein (0.25 µg) significantly improved these responses. Similarly, Table 7 shows that the presence of free LPD protein did not adversely affect the anti-LPD response.

EXAMPLE 4

A Pneumococcal type 14 polysaccharide solution ("Pn14," available from American Type Culture Collection of Rockville, Md.), containing 5 mg Pn14 at a concentration of 5 mg/ml in saline was mixed with 37.5 µl CDAP at a concentration of 100 mg/ml in acetonitrile. Thirty seconds later 75 µl of 0.2 M triethylamine was added. After an additional two minutes, 5 mg of tetanus toxoid ("TT") was added. The tetanus toxoid was added as a 298 µl solution. Additionally, 50 µl of 0.5 M HEPES (pH 8) was added to maintain the mixture at a pH of about 8.

The reaction was quenched after four hours by adding 100 µl of 2 M glycine (pH 8). To produce a fractionated conjugate product, 1 ml of the resulting reaction mixture was passed through a 1×60 cm S400HR gel filtration column, equilibrated with 0.15 M HEPES and 2 mM EDTA (pH 7.3). The void volume fractions were pooled to provide the conjugate product (approximately 6.9 ml). The fractionated conjugate product contained 0.15 mg/ml TT and 0.17 mg/ml Pn14, which corresponds to 0.87 mg TT/mg Pn14. This represents a recovery of about 1.04 mg TT (32% yield) and 1.2 mg Pn14 (36.6% yield).

To produce the unfractionated product (including the conjugate and free protein), the remainder of the resulting reaction mixture mentioned above (approximately 0.56 ml) was dialyzed into HE buffer (a mixture of 0.15 M hydroxyethyl piperazine N'-2-ethane sulfonic acid ("HEPES") and 2 mM ethylenediamine tetraacetate ("EDTA"), pH 7.3). The resulting product (approximately 1.1 ml) contained 1.66 mg/ml TT and 1.6 mg/ml Pn14, which corresponds to 1.03 mg TT/mg Pn14. This represents a recovery of about 1.83 mg TT (102% yield) and 1.76 mg Pn14 (98% yield).

The immunogenicity of these conjugates was then tested. Groups of mice including four balb/c mice/group were primed with an injection containing various specified amounts of the fractionated and unfractionated conjugate products. On Day 14, the mice were bled and boosted with the same immunogen at the same dose. On Day 28, the mice were bled again. The sera was pooled and titered for anti-Pn14 and anti-TT IgG responses, giving the results shown in Table 8.

TABLE 8

| Dose[c] | Anti-Pn14 IgG Titer[a] | | Anti-TT IgG Titer[b] | |
| --- | --- | --- | --- | --- |
| | Fractionated | Unfractionated | Fractionated | Unfractionated |
| 10 µg | 85288 | 102220 | 12778 | 17455 |
| 1 µg | 33948 | 69826 | 5108 | 7505 |
| 0.1 µg | 22584 | 67860 | 4897 | 7881 |

[a]ELISA with a cutoff at 0.1 absorbance units.
[b]ELISA with a cutoff at 0.5 absorbance units.
[c]The dose amount corresponds to the amount of Pn14 polysaccharide administered.

The data above demonstrates that both the anti-Pn14 titers ad the anti-TT titers were higher for the unfractionated material (containing free protein) at all of the dosages tested, as compared to the fractionated material that has the free protein removed. Additionally, this Example demonstrates that the overall yields of both the protein and the polysaccharide are higher for the dialysis treated unfractionated product as compared to the gel filtered fractionated product. Additionally, the unfractionated material is easier and less expensive to produce.

EXAMPLE 5

This Example illustrates coupling of a peptide to a protein-polysaccharide conjugate. First, tetanus toxoid ("TT," available from Sigma) is conjugated to Pn14 polysaccharide (available from American Type Culture Collection of Rockville, Md.) using CDAP. To accomplish this, Pn14 is provided in water at a concentration of 10 mg/ml. CDAP, from a 100 mg/ml stock solution of CDAP in acetonitrile, is added to the Pn14 solution in the amount of 0.75 mg CDAP/mg Pn14. After 30 seconds, an equal volume of 0.2 M triethylamine is added. The pH of the resulting solution is maintained at ~9.0 for an additional two minutes. Thereafter, TT in saline (at 16 mg/ml) is added at 1 mg TT/mg Pn14. After 1 hour, the reaction is quenched by adding 100 µl 2M glycine (pH 8) per ml of solution. After an overnight incubation at 4° C., the conjugate mixture is dialyzed exhaustively against phosphate buffered saline ("PBS") in a 12,000 kDa cutoff dialysis bag.

The total amount of protein is determined using the Lowry assay. The amount of free protein vs. conjugated protein is determined by size-exclusion HPLC on a Beckman SEC G2000 column. Alternatively, gel filtration on a S400HR column (Pharmacia) is performed, and the amount of protein in the conjugate fraction and the free protein fraction is compared with the total protein.

The amount of free and conjugated protein is labeled with a 40× molar excess of SIA coupling reagent (available from Pierce) to total protein for 2 hours in the dark, dialyzed overnight in the dark against PBS plus 0.2 mM ethylenediamine tetraacetate ("EDTA"). LHRH peptide, synthesized with an N terminal cysteine, is made up at 10 mg/ml in water and added at a 40× molar ratio to the conjugate/free protein mixture. After an overnight reaction, the solution is made 0.2 mM in mercaptoethanol and dialyzed exhaustively into PBS.

This procedure provides a purified conjugate mixture including a peptide-protein conjugate and a peptide-protein-polysaccharide conjugate. The LHRH-TT and LHRH-TT-Pn14 conjugate mixture is analyzed as follows. Free peptide is estimated by gel filtration of a mixture on a Superdex peptide column (Pharmacia), monitored at 280 nm, by comparing the peptide peak to a standard amount of free peptide. Alternatively, a reverse phase column can be used to determine the amount of free peptide.

For comparison purposes, the LHRH-TT-Pn14 conjugate can be obtained by gel filtration on a S400HR column (from Pharmacia). The total amount of protein is determined using the Lowry assay. The amount of Pn14 is determined by a resorcinol-sulfuric acid assay (Monsigny, et al., *Anal. Chem.*, Vol. 175, 1988, beginning at page 525).

An ELISA assay is performed to confirm the presence of the LHRH peptide, and the assay results are compared with an LHRH-TT standard of known composition, using a standard anti-sera against LHRH.

Male mice are immunized on Day 0 with 10 µg of protein, either as a mixture of conjugated and unconjugated protein or as a conjugated protein only. On Day 28, the mice are given a booster immunization, and the mice are bled 14 days later and 2 months later. At the later date, the mice are sacrificed, and a histological examination of the testicles is performed. All sera are assayed for anti-LHRH, anti-TT and anti-Pn14, as well as for testosterone.

It is expected that there will be high anti-body titers to all three components and that testosterone levels will progressively decrease due to the presence of anti-LHRH. It also is expected that there will be no sperm.

EXAMPLE 6

Tetanus toxoid is labeled with a 20 fold molar excess of SIA coupling reagent (available from Pierce) for 2 hours in the dark, desalted on a P6DG column (BioRad) equilibrated with 0.15 M hydroxyethyl piperazine N'-2-ethane sulfonic acid ("HEPES") and 0.2 mM EDTA, and concentrated to 15 mg/ml with a Centricon 50 device (Amicon). LHRH peptide, synthesized with an N terminal cysteine, is made up at 10 mg/ml in water and added at a 20× molar ratio to the TT-SIA. After an overnight reaction at 4° C., the reaction solution is made 0.2 mM in mercaptoethanol to quench for one hour, followed by exhaustive dialysis using a membrane with a 14,000 kDa cutoff.

The LHRH-TT is coupled to Pn14 polysaccharide using CDAP as described above in Example 5. Analysis on the resulting LHRH-TT and LHRH-TT-Pn14 conjugate mixture is performed in the same manner as described above in Example 5. The same test results are expected.

This invention further relates to vaccines, immunogens, and other immunological reagents that can be prepared from the protein-polysaccharide conjugates and the hapten-protein-polysaccharide conjugates produced by the methods in accordance with the invention. In a vaccine, immunogen, or other immunological reagent, the conjugates produced by the methods according to the invention can be combined with a pharmaceutically acceptable medium or delivery vehicle by conventional techniques known to those skilled in the art. Such vaccines and immunological reagents will contain an effective therapeutic amount of the conjugate and free protein according to the invention, together with a suitable amount of vehicle so as to provide the form for proper administration to the subject. These vaccines may include alum or other adjuvants.

Exemplary pharmaceutically acceptable media or vehicles include, for example, sterile liquids, such as water and oils, including those of petroleum, animal, vegetable, or synthetic origin, such as peanut oil, soybean oil, mineral oil, sesame oil, and the like. Saline is a preferred vehicle when the pharmaceutical composition is administered intravenously. Aqueous dextrose and glycerol solutions also can be employed as liquid vehicles, particularly for injectable solutions. Suitable pharmaceutical vehicles are well known in the art, such as those described in E. W. Martin, *Remington's Pharmaceutical Sciences*, which reference is entirely incorporated herein by reference.

The invention also relates to the method for treating a subject by administering an immunostimulatory amount of the vaccine. The conjugates according to the invention may be administered to any subject for whom the treatment may be beneficial, including mammals, especially humans, horses, cows, pigs, sheep, deer, dogs, and cats, as well as other animals, such as chickens. An "immunostimulatory amount" refers to that amount of vaccine that is able to stimulate the immune response of the subject for prevention, amelioration, or treatment of diseases. The vaccines of the invention may be administered by any suitable route, but they preferably are administered by intravenous, intramuscular, intranasal, or subcutaneous injection.

In addition, the vaccines, immunogens, or immunological reagents in accordance with the invention can be administered for any suitable purpose, such as for therapeutic, prophylactic, or diagnostic purposes.

In describing the invention, applicants have set forth certain theories in an effort to disclose how or why the invention works in the manner in which it works. These theories are set forth for informational purposes only. Applicants are not to be bound by any specific chemical or physical mechanisms or theories of operation.

While the invention has been described in terms of various preferred embodiments and specific examples, those skilled in the art will recognize that various changes and modifications can be made without departing from the spirit and scope of the invention, as defined in the appended claims.

We claim:

1. A process for preparing a hapten-protein-polysaccharide conjugate, and a hapten-protein conjugate, comprising:
    a) reacting a protein with a polysaccharide to produce a mixture including a protein-polysaccharide conjugate and free protein;
    b) removing at least one unreacted reagent or low molecular weight component from the mixture to step a) to provide a purified mixture that contains the protein-polysaccharide conjugate and free protein; and
    c) reacting a hapten with the purified mixture of step b) to thereby provide a conjugate mixture including a hapten-protein conjugate and a hapten-protein-polysaccharide conjugate.

2. The process according to claim 1, further including removing excess hapten from the conjugate mixture to thereby provide a purified conjugate mixture.

3. The process according to claim 2, wherein the hapten is removed from the conjugate mixture by dialysis to provide the purified conjugate mixture.

4. The process according to claim 3, further including combining the purified conjugate mixture with a pharmaceutically acceptable medium or delivery vehicle.

5. The method according to claim 4, wherein the pharmaceutically acceptable medium or delivery vehicle is at least one member selected from water, petroleum oil, animal based oil, vegetable oil, peanut oil, soybean oil, mineral oil, sesame oil, saline, aqueous dextrose, and a glycerol solution.

6. The process according to claim 1, wherein the hapten is a peptide selected from luteinizing hormone releasing hormone, peptides derived from *E coli*, and malaria derived peptides.

7. A mixture comprising a hapten-protein-pylysaccharide conjugate and hapten-protein conjugate produced by the process of claim 1.

* * * * *

UNITED STATES PATENT AND TRADEMARK OFFICE
CERTIFICATE OF CORRECTION

PATENT NO. : 6,756,041 B2
DATED : June 29, 2004
INVENTOR(S) : Andrew Lees et al.

It is certified that error appears in the above-identified patent and that said Letters Patent is hereby corrected as shown below:

Title page,
Item [74], *Attorney, Agent, or Firm*, "Finnegan, Henderson, Farabow, Garrett and Dunnter, LLP" should read -- Finnegan, Henderson, Farabow, Garrett and Dunner, LLP --.

Column 14,
Line 61, "mixture to" should read -- mixture of --.

Column 16,
Line 8, "hapten-protein-pylysaccharide" should read -- hapten-protein-polysaccharide --.

Signed and Sealed this

Thirty-first Day of August, 2004

JON W. DUDAS
*Director of the United States Patent and Trademark Office*